US006660479B2

(12) United States Patent
Kim et al.

(10) Patent No.: US 6,660,479 B2
(45) Date of Patent: *Dec. 9, 2003

(54) PROCESS FOR PREPARING PEPTIDE NUCLEIC ACID PROBE USING POLYMERIC PHOTOACID GENERATOR

(75) Inventors: Min-Hwan Kim, Taejon (KR); Do-Yun Kim, Taejon (KR); Bong-Seok Moon, Taejon (KR); Jae-Chan Park, Taejon (KR); Young-Hee Kim, Taejon (KR); Seung-Joo Seo, Taejon (KR)

(73) Assignee: Samsung Electronics Co., Ltd., Kyounggi-Do (KR)

( * ) Notice: Subject to any disclaimer, the term of this patent is extended or adjusted under 35 U.S.C. 154(b) by 15 days.

This patent is subject to a terminal disclaimer.

(21) Appl. No.: 10/073,071

(22) Filed: Feb. 7, 2002

(65) Prior Publication Data

US 2002/0122874 A1 Sep. 5, 2002

Related U.S. Application Data

(63) Continuation-in-part of application No. 09/762,611, filed as application No. PCT/KR00/00590 on Jun. 7, 1999, now Pat. No. 6,359,125.

(30) Foreign Application Priority Data

Jun. 7, 1999 (KR) .......................... 1999-20899

(51) Int. Cl.⁷ .......................... C12Q 1/68; C07H 21/00; C07H 21/02; C07H 21/04
(52) U.S. Cl. .......................... 435/6; 536/22.1; 536/23.1; 536/24.3; 536/25.3; 536/25.32; 536/26.3
(58) Field of Search .......................... 435/6; 536/23.1, 536/22.1, 24.3, 25.3, 26.3, 25–32

(56) References Cited

U.S. PATENT DOCUMENTS

| 5,143,854 A | 9/1992 | Pirrung et al. |
| 5,658,734 A | 8/1997 | Brock et al. |
| 5,843,655 A | 12/1998 | McGall |
| 5,866,304 A | 2/1999 | Nakano et al. |
| 6,060,242 A | 5/2000 | Nie et al. |
| 6,359,125 B1 * | 3/2002 | Kim et al. ................. 536/23.1 |
| 6,426,184 B1 * | 7/2002 | Gao et al. ................... 435/6 |

OTHER PUBLICATIONS

Ishii, et al., "Design and Lithographic performances of 193-specific photoacid generators," *Advances in Resist Technology and Processing XVII*, 3999:1120–1127 (2000).
Fodor, et al., "Light–Directed, Spatially Addressable Parallel Chemical Synthesis," *Science*, 51:767–773 (1991).
Anderson, et al., "Polynucleotide Arrays for Genetic Sequence Analysis," *Topics in Current Chemistry*, 194:1–13(1998).

McGall, et al., "The Efficiency of Light–Directed Synthesis of DNA Arrays on Glass Substrates," *J. Am. Chem. Soc.*, 119:5081–5090 (1997).
Beecher, et al., "Chemically Amplified Photolithography for the Fabrication of High Density Oligonucleotide Arrays," *Polymer. Material Science Eng.*, 76:597–598 (1997).
Pease, et al., "Light–generated oligonucleotide arrays for rapid DNA sequence analysis," *Proc. Natl. Acad. Sci. USA*, 91:5022–5026 (1994).
Chee, et al., "Accessing Genetic Information with High–Density DNA Arrays," *Science*, 274:610–614 (1996).
Wang, et al., "Large Scale Identification, Mapping, and Genotyping of Single–Nucleotide Polymorphisms in the Human Genome," *Science*, 280:1077–1082 (1998).
Schena, et al., "Quantitative Monitoring of Gene Expression Patterns with a Complementary DNA Microarray," *Science*, 270:467–470 (1995).
Egholm, et al., "PNA hybridizes to complementary oligonucleotides obeying the Watson–Crick hydrogen–bonding rules," *Nature*, 365:566–568 (1993).
Corey, et al., "Peptide nucleic acids: expanding the scope of nucleic acid recognition," *TIBTECH*, 15:224–228 (1997).
Nielsen, et al., "Peptide Nucleic Acid. A Molecule with Two Identities," *Acc. Chem. Res.*, 32:624–630 (1999).
Gao, et al., "Oligonucleotide Synthesis Using Solution Photogenerated Acids," *J. Am. Chem. Soc.*, 120:12698–12699 (1998).

* cited by examiner

*Primary Examiner*—Jezia Riley
(74) *Attorney, Agent, or Firm*—Knobbe, Martens Olson & Bear, LLP

(57) ABSTRACT

Disclosed is a process for preparing arrays of oligopeptide nucleic acid probes immobilized on a solid matrix by employing polymeric photoacid generator. Arrays of peptide nucleic acid probes of the invention are prepared by the steps of: (i) derivatizing the surface of a solid matrix with aminoalkyloxysilane in alcohol and attaching a linker with acid-labile protecting group on the solid matrix; (ii) coating the solid matrix with polymeric photoacid generator(PAG); (iii) exposing the solid matrix thus coated to light to generate acid for eliminating acid-labile protecting group; (iv) washing the solid matrix with alkaline solution or organic solvent and removing residual polymeric photoacid generator; and, (v) attaching a monomeric peptide nucleic acid with acid-labile protecting group to the solid matrix, and repeating the previous Steps of (ii) to (v). In accordance with the present invention, neutral peptide nucleic acid probes, as the promising substitute for conventional negatively-charged oligonucleotide probes, can be prepared by employing polymeric photoacid generator in a simple and efficient manner, while overcoming the problems confronted in the prior art DNA chip fabrication using PR system and PPA system.

46 Claims, No Drawings

PROCESS FOR PREPARING PEPTIDE NUCLEIC ACID PROBE USING POLYMERIC PHOTOACID GENERATOR

RELATED APPLICATION

This application is a continuation-in-part of U.S. patent application Ser. No. 09/762,611, now allowed, filed Feb. 17, 2001 based on International Application No. PCT/KR00/00590 under 35 U.S.C. §371, which claims foreign priority based on Korean Patent Application No. 1999-20899, filed Jun. 7, 1999. The International Application No. PCT/KR00/00590 was filed Jun. 7, 2000 and published in English as WO 00/75372 A1 on Dec. 14, 2000, which is incorporated herein by reference.

BACKGROUND OF THE INVENTION

1. Field of the Invention

The present invention relates to a process for preparing peptide nucleic acid probes by employing polymeric photoacid generator, more specifically to a process for preparing arrays of oligopeptide nucleic acid probes immobilized on a solid matrix by employing polymeric photoacid generator.

2. Description of the Related Art

Biochips, a kind of biosensor used for genomic analysis, medical diagnosis and monitoring biological processes and environment, are largely classified into DNA chip which identifies nucleotide sequences and protein chip which recognizes proteins such as pathogens, antibodies, antigens or enzymes.

The structure of DNA identified by Watson and Crick in 1953 has been a great impact on life sciences such as molecular biology, biochemistry, etc. DNA is a biopolymer with four different bases of adenine (A), cytosine (C), guanine (G), thymine (T), sugar (deoxyribose) and phosphate, to build a very stable double helix structure: the phosphate-sugar forms backbone, bases attached to the sugar are paired with complementary bases, such as A to T, and G to C, which are stabilized by hydrogen bond. The specific/complementary hydrogen bond between bases plays a very important role in drug developments such as antisense drug and gene therapy, in particular, for genetic disease, cancer and cardiac diseases.

Recently, in line with the great efforts made to identify approximately 100,000 human genes, needs for the methods for providing enormous genomic information as fast as possible for the diagnosis and prevention of genetic disease are increasing. Despite Sanger's DNA sequencing method is improved by polymerase chain reaction and automation, it still remains cumbersome and time-consuming, and requires high cost as well as highly trained personnel. Therefore, alternative method to overcome those shortfalls has been constantly deliberated in the art. By virtue of such needs, there has been a considerable progress in the fabrication and utilization techniques of DNA chips for recent several years.

In general, DNA chip is high-density micro-arrays of known oligonucleotide probes ranging from several hundred to several hundred thousands immobilized on a smaller than one square inch solid surface, such as silica, surface-derivatized glass, polypropylene or activated polyacrylamide. If the target DNA fragments are placed on DNA chip, the target DNA fragments hybridize to the probes on the chip according to the sequence complementarity. Therefore, the sequence of the target DNA can be analyzed by the presence and location of hybridized DNA detected by the optical or radiochemical method. Using the DNA chip aided method, DNA analysis system can be miniaturized such that an extremely small amount of sample DNA can be used for diagnosis, several sequences in a target DNA can be analyzed simultaneously, and thus the genetic information can be obtained in a simple, cost effective and fast manner.

The sequence analysis technique using oligonucleotide DNA chip is an innovative method since it is faster and easier to use for sequencing a target gene than the conventional Sanger's method. The Sanger's sequencing method, which requires the separation of fluorescence- or radioisotope-labeled DNA fragments by gel electrophoresis, is proven to be less satisfactory in light of time-consuming and technical difficulties. On the contrary, sequencing by hybridization (SBH) using oligonucleotide DNA chip employs a principle that by placing fluorescence- or radioisotope-labeled target gene fragments to a DNA chip with oligonucleotide probes, and then simply by washing the chip with solvent, gene fragments complementary to known oligonucleotide probes are attached by hydrogen bond.

Merryfield's synthetic method in which chemical compounds are reacted on organic solvent-resistant solid matrix and further organic reactions are carried out on the solid matrix, has been used effectively in synthesizing oligopeptide of biologically important enzymes and oligonucleotide of genes, since it is very simple and efficient in the purification of reaction products. See Fed. Proc., 24:412, 1962. A new efficient synthetic method combining the said method with combination chemistry has been used effectively for catalyst screening and also been used in drug development as well. In addition, by the combination of the synthetic method on a solid matrix and the photolithography employed in semiconductor industry, various techniques for preparing arrays of oligonucleotide probes have been developed to be used for genetic diagnosis. The said technique comprises selective activation of specific regions of surface derivatized glass to which the oligonucleotide binds chemically. To activate the specific targeted region, the light beam is applied through a transparent region of photolithographic mask made by a predetermined pattern. By controlling the mask pattern and composition of nucleic acids at each step, a specific nucleic acid can be positioned on a desired location. This technique is an ultra-fine processing technique used in semiconductor devices which makes possible several millions of probes be affixed on a fingernail-size chip.

For example, Fordor et al teaches a new direct photolysis technique, where nucleic acid or amino acid with UV-labile protecting group is attached on a solid surface, the protecting group is eliminated by exposing the selected regions of surface to light using photolithographic mask, which is subsequently reacted with a new nucleic acid or amino acid with a photo-labile protecting group, to polymerize nucleic acid or amino acid at specific location. See U.S. Pat. No. 5,445,934, which is hereby incorporated herein by reference. Since this method allows selective synthesis of oligonucleotide probes with a specific sequence/length at a specific location, it is useful in synthesizing various oligonucleotide probes with a desired sequence and length at a predetermined position. Also, since this method employs ultra-fine process used in semiconductor devices, it is extremely useful for fabricating oligonucleotide probes in high density. Fordor et al also suggested that a sequencing method using the oligonucleotide probes which is much easier and faster than Sanger's method, is useful for making high density oligonucleotide probes. However, it has revealed a shortcoming that: the removal of photo-labile protecting group is proportional to the power of a light source, which plays a detrimental role in the ultra-fine process for making high density chips.

On the other hand, photolithographic process using photoresist (hereinafter referred to as 'PR') which is used for micropattern formation in semiconductor industry has attracted attention as an essential technique to improve the density of DNA chip. Since the size or capacity of a semiconductor chip is depending on the spatial resolution of photolithographic process, photolithographic process has played a leading role in the semiconductor and microelectronics industry. The photolithographic process utilizes the solubility differences of PR between the light exposed region and the unexposed region. The solubility reduction in the exposed region is called as negative system and solubility increase is called as positive system, and the latter is used mostly for the production of semiconductor chips. By using above photolithographic process, more oligonucleotide probes can be arrayed on a limited area of chip.

Up to now, photolithographic process has been applied in the general PR system (U.S. Pat. No. 5,658,734) and the photoacid patterned array system (hereinafter referred to as 'PPA', U.S. Pat. No. 5,843,655) as well. The referenced patents are hereby incorporated herein by reference.

Photolithographic process using PR system (hereinafter referred to as 'PR process') has an advantage of using materials already developed or commercialized for semiconductor industry. According to the system, a pattern is formed by the light exposure and washed out to lead to standard solid-phase nucleic acid synthetic reaction on the surface, finally to link nucleotides. The PR includes diazoquinone/cresol-novolac, highly adhesive to the surface, which is shown to have good pattern characteristics in i-line (365 nm) and used in 16 mega DRAM processing. However, the PR is developed in alkaline solution ([OH-]>0.1M), that causes the cleavage of amide bond protecting the amino group of base. The protecting coating under PR has been suggested to overcome the said problem of development. See J. Vac. Sci. Tech., B7(6):1734 (1989), which is hereby incorporated herein by reference.

PR process is consisted of three major steps: the first is mainly the PR pattern formation with PR coating, light exposure and developing; the second is the removal of protecting group and unexposed area by acidic solution; and, the third is the attachment of nucleic acid and post-treatment. Photolithographic process using PR system is good enough for obtaining high resolution, but complex processing as described above has been a major drawback.

To simplify the complex process and improve the efficiency, the PPA system has been proposed in the art. Since the PPA system uses polymeric matrix mixed with photoacid generator (hereinafter referred to as 'PAG'), acids are generated only at the exposed region and removal of protecting group occurs after heat treatment, therefore the two separate steps employed in PR processing can be carried out in one step. However, this PPA system has revealed several problems as well. For example, while PR process is not affected by the concentration or volume of the acid solution since it uses large volume of acid solution to contact and to remove the protecting group, acid generated by the PPA system remains on the polymeric matrix and, to balance the amount of acid, more PAG should be added. However, at above a certain level of PAG, PAG domain forms and scatters light which in turn interferes with micro pattern formation. In other words, excessive amount of PAG which is used for stability and reproducibility of the pattern formation reduces the efficiency of processing. In addition, the generated acid should diffuse from the polymer to the surface (actually closer to the heat source) of the protecting group by heat, but the generated acid, when the glass plate is heated on a hot plate, may diffuse to the opposite direction from the protection group, thereby reducing the efficiency. Furthermore, the mixed film of polymer and PAG for coupling, has to be removed by organic solvent such as acetone or methylethylketone, which makes the progress more expensive.

Another problem confronted in the art DNA chip techniques is the reduction of degrees of the association/dissociation, speed in the course of hybridization of oligonucleotide probes with target genes and point mutations present in a gene. For example, Nielsen et al developed neutrally charged peptide nucleic acid (hereinafter referred to as 'PNA') to replace oligonucleotides which can be synthesized by the modified Marryfield's peptide synthesis method, based on the findings that the repulsive force between negatively-charged oligonucleotides reduces the annealing strength as well as speed during hybridization of oligonucleotides. PNA's are biopolymer molecules having a peptide-bonded backbone, to which bases of nucleic acids are connected. PNA greatly improved the association power, and speed during hybridization with oligonucleotide and it is practically applied in detecting single base mutation in a particular gene, which can be realized by the reduced association between non-complementary oligonucleotide. See Nature, 8:53 (1993), which is hereby incorporated herein by reference. Due to this positive characteristic, the antisense drug using PNA is under investigation. However, despite the benefits, there has been no report of using PNA on high density peptide nucleic acid probe synthesis by photolithographic process.

Therefore, there are strong reasons for developing and exploring alternative method for synthesizing peptide nucleic acid as well as oligonucleotide with various nucleotide sequences on a solid matrix, while overcoming the problems confronted in the prior art DNA chip fabrication using PR and PPA system.

SUMMARY OF THE INVENTION

The present inventors made an effort to provide an efficient method for preparing peptide nucleic acid probes with various nucleotide sequences, and developed a highly efficient process for preparing arrays of peptide nucleic acids, which can eliminate the repulsion problem associated with negatively charged oligonucleotide, immobilized on a solid matrix by employing polymeric photoacid generator (hereinafter referred to as 'polymeric PAG') while overcoming the problems of the prior art PPA process employing PAG in polymer.

One aspect of the present invention is to provide a process for manufacturing an array of probes connected to a solid surface. The process comprises: providing a substrate having a surface, wherein a functional group protected by an acid-labile protection group is connected to the surface; deprotecting the functional group connected to the surface; and reacting the deprotected functional group with a compound comprising an element of a probe, thereby connecting the element of the probe to the surface. The provision of the substrate in the process comprises: providing a surface without the functional group; and modifying the surface so as to connect the functional group protected by the acid-labile protection group.

The modification of the surface comprises: connecting an amino group to the surface as the functional group; and protecting the amino group with the acid-labile protection group. Here, the protection of the amino group comprises contacting the amino group connected to the surface with one or more compounds selected from the group consisting of aminoalkylcarboxylic acid, amonoalkoxycarboxylic acid and aminoalkanoylcarboxylic acid with the amino group connected to the surface. The process further comprises capping an unprotected amino group after the protection. The capping comprises contacting a compound comprising an acetyl group with the surface of the substrate. The modification comprises: contacting a compound comprising the functional group with the surface to connect the functional group to the surface; and further contacting a compound comprising the acid-labile protection group with the surface to protect the functional group.

The protected functional group is connected to the surface via one or more elements of the probe. The surface of the substrate is of organic solvent resistance. The substrate is of one or more materials selected from the group consisting of silicon, glass, polyethylene, polypropylene, acrylamide and polymethylmetacrylate. The functional group is an amine. The acid-labile protection group is one ore more selected from the group consisting of t-butyloxycarbonyl, triphenylmethyl, p-anisolyldiphenylmethyl, or di(p-anisolyl)monophenylmethyl The deprotection of the functional group is performed over at least a partial area of the surface. The deprotection of the functional group comprises: coating a composition over the surface connected to the protected functional group, wherein the composition is configured to generate an acid when exposed to light; and exposing the coated composition to light so as to generate the acid, whereby the generated acid contacts the acid-labile protection group. The deprotection further comprises enhancing acid generation. The enhancing the acid generation comprises heating the substrate before the exposure, after the exposure or both. The deprotection further comprises removal of the generated acid. The exposure of the coated composition to light is performed over at least a partial area of the coat of the composition. The exposure of the coated composition to light comprises passing the light through a photomask before it reaches the coated composition. The photomask is configured to allow passage of the light through one or more predetermined openings. The composition for coating is a polymer. The coating comprises spin-coating the surface with the coating composition at a rotational speed of about 1000 to about 5000 rpm. The deprotection further comprises removing the separated protection group from the surface.

The probe comprises a sequence of bases selected from the group consisting of adenine, cytosine, guanine, thymine and uracil. The element of the probe comprises one or more bases selected from the group consisting of adenine, cytosine, guanine, thymine and uracil. The element further comprises an amino group protected by acid-stable protection group. The acid-stable protection group is one or more selected from the group consisting of diphenylmethyloxycarbonyl, benzyloxycarbonyl, p-methoxybenzoyl, benzoyl, phenoxyacetyl, t-butylphenoxyacetyl and isobutanoyl groups. The compound comprising the probe element comprises a monomeric peptide nucleic acid.

The process further comprises washing the substrate after the deprotection. The substrate is washed with an alkaline solution or an organic solvent. The process further comprises capping the deprotected functional group unreacted in the reaction. The compound comprising the probe element further comprises a functional group protected by an acid-labile protection group, and wherein the functional group is connected to the element. The process further comprises: deprotecting the functional group connected to the element that is connected to the surface; and reacting the deprotected functional group connected to the element with another compound comprising an element of the probe, thereby connecting the element connected to the surface and the other element.

Another aspect of the present invention is an array of probes connected to a solid surface manufactured by the above-discussed process.

Still another aspect of the present invention is an intermediate construction of an array of probes connected to a solid surface for producing a biochip. The construction comprises: a solid substrate having a surface; an element of a probe connected to the surface, wherein the element is further connected a functional group protected by an acid-labile protection group; and a coat of a composition over the surface and the element connected to the surface, wherein the composition is configured to generate an acid when exposed to light. In the construction, the surface of the substrate is of organic solvent resistance. The substrate is of one or more materials selected from the group consisting of silicon, glass, polyethylene, polypropylene, acrylamide and polymethylmetacrylate. The element is connected to the surface via one or more elements of the probe. The connection of the element with one or more other elements connected to the surface is in a peptide bond. The probe comprises a peptide nucleic acid (PNA). The probe comprises a sequence of bases selected from the group consisting of adenine, cytosine, guanine thymine, and uracil. The element of the probe comprises one or more bases selected from the group consisting of adenine, cytosine, guanine, thymine and uracil. The element further comprises an amino group protected by acid-stable protection group. The acid-stable protection group is selected one or more from the group consisting of diphenylmethyloxycarbonyl, benzyloxycarbonyl, p-methoxybenzoyl, benzoyl, phenoxyacetyl, t-butylphenoxyacetyl and isobutanoyl groups. The composition for coating is a polymeric photo-acid generator. An acid generated from the composition exists in at least a partial area of the composition coat.

A further aspect of the present invention provides a process of synthesizing a plurality of chemical compounds on a solid surface. The process comprises providing a solid surface; modifying the surface so as for a plurality of a functional group protected by an acid-labile protection group is connected to the surface; coating a layer of photo-acid generator over the modified surface; selectively exposing the coated layer to light, whereby the photo-acid generator generates an acid, which contacts and removes one or more acid-labile protection groups; and contacting molecules for connecting to the surface with one or more functional groups from which the acid-labile groups are removed.

DETAILED DESCRIPTION OF THE PREFERRED EMBODIMENT

The peptide nucleic acid probes with various nucleotide sequences are prepared by derivatizing the surface of a solid matrix with aminoalkyloxysilane in alcohol and attaching a linker with acid-labile protecting group on the solid matrix, coating the solid matrix with polymeric photo acid generator (PAG), exposing the solid matrix thus coated to light to generate acid for eliminating acid-labile protecting group, washing the solid matrix with alkaline solution or organic solvent and removing residual polymeric photo acid generator, and, attaching a monomeric peptide nucleic acid with acid-labile protecting group to the solid matrix, and repeating the previous steps.

Polymeric PAG employed in the invention is a polymer with molecular weight of 500 to 1,000,000, which has sulfonium salt on backbone or side chain, and has also organic photo-acid generating group on side chain to generate acid by exposing to light.

The peptide nucleic acid monomers of the invention has N-(2-aminoethyl) glycine backbone to which adenine, cytosine, guanine, thymine or uracil base is linked by amide bond. Peptide nucleic acids are synthesized by amide bond between an amino group of backbone and a carboxyl group of other peptide nucleic acid monomer. Currently, peptide nucleic acid monomers protected by acid-labile t-butyloxycarbonyl protecting group or alkali-labile fluoromethyloxycarbonyl protecting group are commercially available, where exocyclic amino groups of adenine, cytosine and guanine are protected by acid-stable diphenylmethyloxycarbonyl or benzyloxycarbonyl protecting group. The present inventors employed monomers whose amino groups of backbone are protected by acid-labile t-butyloxycarbonyl, and synthesized bases whose exocyclic amino groups are protected by stable p-methoxybenzoyl or isobutanoyl group.

The peptide nucleic acid synthesis method is generally carried out in a similar manner as the oligonucleotide synthesis method conventionally known in the art. See Acc. Chem. Res., 24:278 (1991), which is hereby incorporated herein by reference. Nielson et al synthesized oligopeptide nucleic acid by using solid-phase phase as follows: First, the amino group of solid support is reacted with the carboxyl group of peptide nucleic acid of specified base (A, C, G or T) whose amino group in backbone is protected by acid- or base-labile functional group to link each other in a form of amide bond. Next, the resultant is treated with acid or base to eliminate amino protecting group to reveal amino group, which is subsequently reacted with the carboxyl group of peptide nucleic acid of specified base whose amino group in backbone is protected by acid- or base labile functional group to link each other in a form of amide bond, and, the said steps are repeated to obtain an oligopeptide of desired base sequence and number, and finally treated with strong acid to separate the exocyclic amino protecting group from solid support by chemical reaction. This method is desirable in a sense that it assures complete reaction of excessive peptide nucleic acids (5 equivalents) as much as possible and easy purification of peptide nucleic acid on an organic solvent-resistant solid support by filtering the residual monomers and reactants and washing with organic solvent. Based on the solid-phase synthesis, the present inventors prepared biochip with various nucleotide sequences to finally prepare arrays of peptide nucleic acid probes immobilized on a solid matrix by employing polymeric PAG process illustrated above.

The polymeric PAG and peptide nucleic acid monomer which are employed in the process of preparing peptide nucleic acid probes with various nucleotide sequences were prepared by Preparative Examples 1 and 2, and Preparative Example 3, respectively.

Preparative Example 1

Polymeric PAG in Chloride Salt Form 0.026 Mole of anisol diphenol sulfide salt was dissolved in 26 ml of N,N'-dimethylacetamide, added 0.077 mol of triethylamine, then cooled to 0° C. To 0.026 mol of sebaconylchloride in 26 ml of heptane, was added the said solution, and reacted overnight at room temperature. After the top layer of heptane was separated and gently removed from the mixture, the N,N'-dimethylacetamide layer was added in a dropwise to 400 ml of diethylether to obtain the precipitate. The polymeric PAG in chloride salt form was obtained by filtering and drying the precipitate. The material thus obtained was resolubilized in 20 ml of methanol, re-precipitated in water, and then filtered and dried to obtain the titled compound.

Preparative Example 2

Substitution of Salt

Preparative Example 2-1 p-Toluenesulfonic Salt of Polymeric PAG 0.01 Mole of polymeric PAG in chloride salt form obtained in Preparative Example 1 was dissolved in 10 ml of methanol, added 0.03 mol of p-toluenesulfonic acid in sodium salt form. After 3 hours' incubation, the solution was concentrated by removing 7 ml of methanol and precipitated by adding water. The precipitate was filtered and dried to obtain p-toluenesulfonic acid salt of polymeric PAG.

Preparative Example 2—2

Naphtol Sulfonic Acid Salt of Polymeric PAG 0.01 Mole of polymeric PAG in chloride salt form obtained in Preparative Example 1 was dissolved in 10 ml of methanol, then added 0.03 mol of 1-naphthol-5-sulfonic acid in sodium salt form. After 3 hours' incubation, the solution was concentrated by removing 7 ml of methanol and precipitated by adding water. The precipitate was filtered and dried to obtain 1-naphthol-5-sulfonic acid salt of polymeric PAG.

Preparative Example 2-3

9,10-Dimethoxy-2-anthracene Sulfonic Salt of Polymeric PAG 0.01 Mole of polymeric PAG in chloride salt form obtained in Preparative Example 1 was dissolved in 10 ml of methanol, then added 0.012 mol of 9,10-dimethoxy-2-anthracene sulfonic acid salt. After 3 hours' incubation, the solution was concentrated by removing some methanol and precipitated by adding water. The precipitate was filtered and dried to obtain 9,10-dimethoxy-2-anthracene sulfonic acid salt of polymeric PAG.

Preparative Example 3

Peptide Nucleic Acid Monomer

Preparative Example 3-1

Peptide Nucleic Acid Backbone

In a 2 liter round flask, 107 ml (1.60 mol) of ethylenediamine and 60 ml of 1,4-dioxane were mixed with stirring. Then, 600 ml of di-t-butylcarbonate solution (43.65 g (0.20 mol) in 1,4-dioxane) was added and incubated overnight with constant stirring. Then, the solvent was evaporated under reduced vacuum and added 1 liter of water to the remaining solution. The white precipitate generated by addition of water was removed by filtering and extracted with dichloromethane. Organic phase layer thus obtained was pooled and dried with magnesium sulfate, and concentrated under reduced vacuum to obtain 27.21 g (1.36 mol) of t-butyl N-(2-aminoethyl) glycinate, white powder. 5.00 g (0.25 mol) of t-butyl N-(2-aminoethyl) glycinate was dissolved in 500 ml of dichloromethane in a 2 liter reaction flask, then added 41.5 ml (0.30 mol) of triethylamine at once, and added 62.54 g (0.27 mol) of benzyl-2-bromoacetate in a dropwise, and incubated overnight with constant stirring. The resultant was then extracted with dichloromethane, washed with water and brine in a serial manner. Then, the resulting organic phase layer was dried with magnesium sulfate, and concentrated under reduced vacuum to obtain crude compound. The crude compound was fractionated with silica gel column chromatography by using a mobile phase of 5% methanol/dichloromethane, and 47.80 g (0.16 mol) of benzyl N-[2-(t-butoxyl)aminoethyl] glycinate was obtained in a white powder form.

$^1$H NMR(CDCl$_3$) δ7.39(s, 5H), 5.18(s, 2H) 5.01(br s, 1H), 3.5(s, 2H) 3.25(t, 2H ), 2.78(t, 2H), 1.45(s, 9H)

Preparative Example 3-2

Adenine Monomer

After 27.03 g (0.20 mol) of adenine was dissolved in 500 ml of pyridine, 34.12 g (0.20 mol) of p-anisole chloride was added slowly over 55 minutes, and reacted for 4 hours at 100° C. with stirring. Then, the reaction temperature was lowered to room temperature, further reacted overnight with constant stirring, and removed pyridine by distilling under reduced vacuum. The resulting crude compound was recrystallized in isopropanol and methanol respectively, to give 33.7 g (0.13 mol) of white powder of $N^6$-(4-methoxybenzoyl) adenine. 33.66 g (125 mmol) of $N^6$-(4-methoxybenzoyl) adenine and 400 ml of DMF were placed in a 1 liter reaction flask, added 6.0 g (150 mmol) of 60% NaH slowly, added 22.15 ml (150 mmol) of t-butylbromoacetate in a dropwise over 1 hour 15 minutes, and then, reacted overnight. The reaction solvent, DMF was removed under reduced vacuum, and the precipitate was obtained after addition of water. The precipitate was separated and recrystallized in methanol to obtain 33.46 g (87.30 mmol) of $N^6$-(4-methoxybenzoyl)-9-(t-butoxycarbonylmethyl) adenine as a white solid. In a 2 liter reaction flask, 33.46 g (87.30 mmol) of $N^6$-(4-methoxybenzoyl)-9-(t-butoxycarbonylmethyl) adenine and 800 ml of dichloromethane were placed, mixed at room temperature, and added 180 ml of TFA. The reactants were mixed overnight at the same temperature with constant stirring. After dichloromethane and TFA were removed under reduced vacuum, the resulting crude compound was solublized in 450 ml of 1N NaOH. The solution was washed with dichloromethane and acidified with 6N HCl to obtain 23.54 g (71.9 mmol) of $N^6$-(4-methoxybenzoyl)-9-(carbonylmethyl) adenine as white solid. In a 500 ml reaction flask, 21.99 g (67.20 mmol) of $N^6$-(4-methoxybenzoyl)-9-(carbonylmethyl) adenine, 20.72 g (62.7 mmol) of benzyl N-[2-(t-butoxyl)aminoethyl]glycinate and 200 ml of dichloromethane were added sequentially, and then added 14.17 g (73.92 mmol) of 1-(3-dimethylaminopropyl)-3-ethylcarbodiamide at once. The reaction mixture was incubated overnight at room temperature with constant stirring, extracted with dichloromethane and water, and washed with brine. The organic phase layer was dried with magnesium sulfate, and concentrated under reduced vacuum to obtain crude compound, which was subsequently purified through flash column chromatography by using a mobile phase of 5% methanol/dichloromethane to give 28.24 g (45.70 mol) of benzyl N-[2-(t-butoxylcarbonyl)aminoethyl]-N-[(N$^6$-(4-methoxybenzoyl)-adenine-9-yl)acetyl]glycinate as a white powder. 400 ml of methanol was added to 28.24 g (45.70 mol) of the said compound, and then added 1.0 g of palladium on activated carbon(Pd/C) with stirring. Under hydrogen environment created by hydrogen balloon, the reaction flask was stirred for 3 hours. The catalyst was removed by filtering though celite, and evaporated the solvent under reduced vacuum. The resultant material was solubilized in 200 ml of 1N NaOH, washed with dichloromethane, acidified with 6N HCl and recrystallized in dichloromethane and hexane, respectively, to obtain 17.07 g (32.40 mmol) of N-[2-(t-butoxycarbonyl)aminoethyl]-N-[(N$^2$-(4-methoxybenzoyl)-adenine-9-yl) acetyl]glycine (white powder) as a titled product.

$^1$H NMR(DMSO-D$_6$) δ11.0(s, 1H), 8.67(s, 1H), 8.30(S, 1H), 8.05(d, 2H), 7.08(d, 2H), 5.16(2×s, 2H), 3.98(2×s, 2H), 3.84(s, 3H), 3.04(m, 1H), 1.38(s, 9H)

Preparative Example 3—3

Guanine Monomer

After 3.02 g (20 mmol) of guanine was added into 60 ml of DMF, 6.2 ml (44 mmol) of triethylamine and 4.6 ml (44 mmol) of isobutylyl chloride were added, and the reaction was carried out overnight at 120° C. with constant stirring. Then, the reaction temperature was lowered to room temperature and the reaction was stopped by addition of 20 ml of methanol. The reaction solution was concentrated under reduced vacuum, and precipitated by adding hot isopropanol. The precipitate was filtered and separated to obtain 1.84 g (8.32 mmol) of $N^2$-(isobutanoyl) guanine as a white powder. To 1.83 g (8.27 mmol) of $N^2$-(isobutanoyl) guanine, was added 50 ml of DMF and 0.40 g (10 mmol) of 60% NaH. The resulting suspension was stirred for 1 hour at room temperature, added 1.35 ml (9.14 mmol) of t-butylbromoacetate and mixed with constant stirring for 2 more hours at the same temperature. The resulting solution was then treated with CO$_2$/methanol, concentrated under reduced vacuum to obtain the crude compound. The crude compound was extracted with ethylacetate, and the resulting organic phase layer was concentrated under reduced vacuum to give a mixture of $N^2$-(isobutanoyl)-9-(t-butoxycarbonylmethyl) guanine and $N^2$-(isobutanoyl)-7-(t-butoxycarbonylmethyl) guanine as a white powder. To the mixture, were added 50 ml of dichloromethane and 19 ml of TFA with stirring. The final reaction mixture was incubated for 2 days with constant stirring, and concentrated under reduced vacuum, to obtain a mixture of 1.5 g (5.64 mmol) of $N^2$-(isobutanoyl)-9-(carboxylmethyl) guanine and $N^2$-(isobutanoyl)-7-(carboxylmethyl) guanine. The said mixture was treated with ethylacetate to give a white precipitate, and filtered and dried under reduced vacuum, to give 0.72 g (2.57 mmol) of $N^2$-(isobutanoyl)-9-(carboxylmethyl) guanine. 690 mg (2.47 mmol) of the said compound, 922 mg (2.99 mmol) of benzyl N-[2-(t-butoxyl)aminoethyl] glycinate and 577 mg (3.01 mmol) of EDC were dissolved in 20 ml of DMF, and the reaction mixture was stirred for 3 hours at room temperature with constant stirring. After DMF was removed under reduced vacuum, the resultant compound was extracted with ethylacetate, and the organic phase layer was concentrated under reduced vacuum. The crude compound was solubilized in 10 ml dichloromethane, and recrystallized in hexane to obtain white precipitate. The precipitate was separated and further purified through flash column chromatography by using a mobile phase of 10% methanol/dichloromethane to give 1.24 g (2.18 mmol) of benzyl N-[2-(t-butoxylcarbonyl)aminoethyl]-N-[(N$^2$-

(isobutanoyl)-guanine-9-yl)acetyl]glycinate. 25 ml of methanol was added to 1.22 g (2.14 mmol) of said compound, and then mixed with 0.25 g of 10% Pd/C with stirring. Under hydrogen environment created by hydrogen balloon, the reaction flask was stirred for 2 hours and 45 minutes. The catalyst was removed by filtering though celite, and the filtrate was concentrated under reduced vacuum. The crude compound was dissolved in ethylacetate and stirred overnight to obtain a white precipitate. The precipitate was filtered and dried to obtain 0.92 g (1.91 mmol) of N-[2-(t-butoxylcarbonyl)aminoethyl]-N-[(N$^2$-(isobutanoyl)-guanine-9-yl)acetyl]glycinate in a white powder form.

$^1$H NMR(DMSO-D$_6$) δ7.82(2xs, 1H), 7.03~6.81(m, 2H), 4.94(2xs, 2H), 3.99(2xs, 2H), 3.04(d, 1H), 3.19(2xt, 2H), 2.89(t, 2H), 2.78(m, 1H) 1.19(d, 6H)

Preparative Example 3-4

Cytosine Monomer 22.02 g (0.20 mol) of cytosine was dissolved in pyridine, added 37.53 g (0.22 mol) of p-anisole chloride slowly over 45 minutes. Then, the reaction temperature was slowly elevated to 120° C., and reacted overnight at the same temperature with constant stirring. The crude product was obtained by concentrating the resultant under reduced vacuum. The crude product was then solubilized in methanol, heated and cooled to obtain the precipitate. The precipitate was filtered and dried to obtain 25.78 g (0.11 mol) of N$^4$-(4-methoxybenzoyl) cytosine. To 25.75 g (0.11 mol) of N$^4$-(4-methoxybenzoyl) cytosine in a 1 liter reaction flask was added 500 ml of DMF, then added 5.04 g (0.13 mol) of 60% NaH and 18.61 ml (0.13 mol) of t-buthylbromoacetate sequentially. After the reaction mixture was stirred overnight at room temperature, DMF was removed under reduced vacuum. The crude product thus obtained was recrystallized in methanol to obtain 22.52 g (62.60 mmol) of 1-(t-butoxycarbonylmethyl)-N$^4$-(4-methoxybenzoyl)cytosine as a white powder. 22.52 g (62.60 mmol) of the said compound and 600 ml of dichloromethane were put into a 2 liter reaction flask, mixed at room temperature, and then added 130 ml of TFA. The reaction mixture was stirred overnight at room temperature. After dichloromethane and TFA were removed under reduced vacuum, the resulting crude compound was solubilized in 450 ml of 1N NaOH, acidified with 6N HCl to obtain a white precipitate. The precipitate was filtered and dried to obtain 18.82 g (62.10 mmol) of 1-(carboxylmethyl)-N$^4$-(4-methoxybenzoyl) cytosine as a white powder. 18.82 g (62.10 mmol) of the said compound was mixed with 12.05 g (68.3 mmol) of benzyl N-[2-(t-butoxylcarbonyl)aminoethyl] glycinate in a 500 ml reaction flask, and then sequentially with 120 ml of DMF and with 13.09 g (68.30 mmol) of EDC. The reaction mixture was stirred overnight at room temperature, and then DMF solvent was removed under reduced vacuum. The resulting crude product was extracted with dichloromethane, concentrated under reduced vacuum, and recrystallized in dichloromethane and hexane, respectively. 26.90 g (45.30 mmol) of benzyl N-[2-(t-butoxycarbonyl)aminoethyl]-N-[(N$^4$-(4-methoxybenzoyl)-cytosine-1-yl) acetyl]glycinate was obtained as a white precipitate. 26.90 g (45.30 mmol) of the said compound was dissolved in 850 ml of methanol, and then added 1.0 g of Pd/C with stirring. The reaction solution was stirred for 4 hours under hydrogen environment created by hydrogen balloon. The catalyst was removed by filtering though celite, and the filtrate was concentrated under reduced vacuum. The resulting material was then solubilized in 200 ml of 1N NaOH, washed with dichloromethane, acidified with 6N HCl, recrystallized in dichloromethane and hexane, respectively, to obtain 18.83 g (37.40 mmol) of N-[2-(t-butoxycarbonyl)aminoethyl]-N-[(N$^4$-(4-methoxybenzoyl)-cytosine-1-yl) acetyl]glycine as a white powder.

$^1$H NMR(DMSO-D$_6$) δ8.03(d, 2H), 7.95(2xs, 1H), 7.30 (2xs, 1H), 7.04(d, 2H), 4.84~4.66(2xs, 2H), 4.20~3.98(2xs, 2H), 3.82(s, 3H), 3.22~3.03(t, 4H), 1.37(s, 9H)

Preparative Example 3-5

Thymine Monomer

After 50.45 g (0.40 mol) of thymine, 55.28 g (0.40 mol) potassium carbonate and 1.20 ml of DMF were mixed in a 2 liter round flask, 44.40 ml (0.40 mol) of ethylbromoacetate was added at once to the resulting white suspension, and stirred for 48 hours at room temperature. The unsolubilized solid was removed by filtering, and DMF in the filtrate was eliminated under reduced vacuum. After the precipitate was formed by lowering the reaction temperature to 0° C., this precipitate was mixed with 400 ml of water and 11 ml of 6N HCl for 30 minutes with stirring. The white precipitate of 1-(ethoxycarbonylmethyl)thymine was obtained by filtering. The said compound was then mixed with 400 ml of water and 200 ml of 2N NaOH in a 1 liter reaction flask, and refluxed for 10 minutes with heating. When the white suspension solution became clear during heating, the reaction solution was cooled down to 0° C., and added 90 ml of 6N HCl to give a white precipitate. The said precipitate was filtered, washed with water, and dried in vacuum oven to obtain 47.56 g (0.26 mol) of 1-(carboxymethyl)thymine as a white powder. 10.94 g (54.40 mmol) of the said compound and 15.27 g (49.50 mmol) of benzyl N-[2-(t-butoxycarbonyl)aminoethyl]glycinate were then dissolved in 250 ml of DMF. And then, 11.39 g (59.40 mmol) of EDC was added and stirred overnight at room temperature. After DMF in the reaction solution was removed under reduced vacuum, 500 ml of water was added to the remaining solution and extracted with dichloromethane. The resulting organic phase was dried with magnesium sulfate, concentrated under reduced vacuum to obtain crude compound. The crude compound was purified through flash column chromatography by using a mobile phase of 10% methanol/dichloromethane to give 21.76 g (45.90 mmol) of benzyl N-[2-(t-butoxycarbonyl)aminoethyl]-N-((thymine-1-yl) acetyl]glycinate as a white powder. 21.76 g (45.90 mmol) of the said compound was dissolved in 400 ml of methanol, and mixed with 10% of 5.0 g Pd/C. Then, the reaction mixture was further stirred under hydrogen environment created by hydrogen balloon for 4 hours and 30 minutes. The catalyst was removed by filtering though celite, and the filtrate was added with 50 ml of 1N NaOH and 100 ml of water, followed by washing with dichloromethane and acidification with 6N HCl. The resulting mixture was extracted with ethylacetate. The organic phase was collected, dried with magnesium sulfate, and concentrated under a reduced vacuum, then further dried in a vacuum oven to obtain 17.05 g (43.60 mmol) of N-[2-(t-butoxycarbonyl)aminoethyl]-N-(thymine-1-yl)acetyl]glycine in a white powder form.

$^1$H NMR(DMSO-D$_6$) δ11.30(d, 1H), 7.30(2xs, 1H), 4.64~4.46(2xs, 2H), 4.19~4.01(2xs, 2H), 3.34(s, 2H), 3.38~3.30(t, 2H), 3.17~2.89(t, 2H), 1.91(s, 3H), 1.37(s, 9H)

The process for preparing arrays of peptide nucleic acid with various nucleotide sequences using polymeric photoacid generator will be illustrated in more detail.

Step 1: Attachment of Linker on the Solid Matrix

The surface of a solid matrix is derivatized with aminoalkyloxysilane in alcohol, and the linker with acid-labile protecting group is attached on the solid matrix.

First, to fix amine group on the surface of solid matrix, e.g., plate made of material containing the organic solvent resistance such as silicon, surface-derivatized glass, polypropylene, or activated acrylamide, preferably surface-derivatized glass, more preferably glass plate for microscope, the solid matrix is immersed in 0.05 to 0.15% (v/v), most preferably 0.1%(v/v) of aminoalkyloxysilane solution, preferably aminopropyltriethoxysilane in alcohol (most preferably, in ethanol), mixed for 3 to 7 minutes, more preferably 5 minutes, at room temperature, washed with alcohol, most preferably ethanol, and dried in the vacuum oven at 100 to 140° C., more preferably at 110 to 130° C., most preferably 120° C., for 10 to 30 minutes, preferably 15 to 25 minutes, most preferably 20 minutes. Then, it is placed under argon gas for 10 to 14 hours, most preferably for 12 hours, immersed in DMF, and washed thoroughly with dichloromethane.

Secondly, to attach the linker with acid-labile protecting group to the amine group fixed on the solid matrix, 0.02 to 0.2 mM, most preferably 0.1 mM of aminoalkylcarboxylic acid solution, most preferably 6-N-t-butoxycarbonylamino carproic acid, in N-methylpyrrolidone containing 0.05 to 0.5 mM, more preferably 0.2 mM of diisopropylethylamine is prepared, and mixed with 0.05–0.5 mM, most preferably 0.12 mM of HATU (o-(7-azabenzotriazol-1-yl)-1,1,3,3-tetramethyluroniumhexafluoro-phosphate) in NMP. After mixing the above two solutions, it is activated for 1 to 5 minutes, most preferably for 2 minutes, the solid matrix thus prepared is immersed and incubated for 30 minutes to 4 hours, preferably 1 to 3 hours, most preferably 2 hours, at 40 to 90° C., most preferably 60° C., with agitation. The unreacted amine group on the solid matrix is capped with acetyl group by incubating in 1:2 to 1:4 (v/v), most preferably 1:3(v/v) of acetic anhydride/pyridine solution for 0.5 to 2 hours, most preferably 1 hour, with agitation.

Step 2: Coating with Polymeric PAG

The solid matrix thus prepared is coated with polymeric PAG: the solid matrix to which the linker or monomer is attached is spin-coated with 5 to 50%(w/v) polymeric PAG in organic solvent, most preferably NMP, at 1,000 to 5,000 rpm, most preferably 3,000 rpm.

Step 3: Removal of Acid-labile Protection Group

The solid matrix thus coated is exposed to light to generate acid, to eliminate acid-labile protection group: the coated solid matrix is soft-baked for 1 minute at 50 to 100° C., most preferably for 30 seconds to 2 minutes at 80° C., and exposed to white light of short wavelength for 6 seconds to 2 minutes, most preferably for 1 minute, using photomask, baked again for 3 minute at 50 to 100° C., most preferably for 30 seconds to 5 minutes at 80° C. to generate acid, finally to remove protecting group at the exposed location selectively.

Step 4: Removal of Residual Polymeric PAG

The solid matrix thus prepared is washed with alkaline solution or organic solvent, and residual polymeric PAG is removed: after completing the Step 3, residual polymeric PAG is washed and removed with diluted trialkylammoniumhydroxide, NaOH solution, KOH solution or organic solvent.

Step 5: Reaction with Peptide Nucleic Acid Monomer

A monomeric peptide nucleic acid with acid-labile protecting group is attached to the solid matrix thus prepared: the selectively exposed amine group on the solid matrix is reacted with the peptide nucleic acid monomer prepared in Preparative Example 3. An NMP solution of 10–20 μM of peptide nucleic acid monomer, most preferably 15 μM, with diisopropylethylamine at a ratio of 1:1 to 1:5(w/w) to the solubilized nucleic acid monomer, and another NMP solution containing HATU at a ratio of 1:1 to 1:2(w/w) to the solubilized nucleic acid monomer in the said mixed solution are prepared. The two solutions are mixed, activated for 1 to 5 minutes, and reacted with the solid matrix thus prepared at 50 to 100° C., most preferably at 60° C. for 1 to 3 hours, most preferably for 2 hours, with agitation. The unreacted amine group is capped with acetyl group by incubating in 1:2 to 1:4(v/v), most preferably 1:3(v/v), of acetic anhydride/pyridine solution for 0.5 to 2 hours, most preferably 1 hour, with agitation.

Then, arrays of peptide nucleic acid probes immobilized on the solid matrix are finally prepared by repeating Steps 2 to 5.

The free reactive group on the solid matrix, i.e. the amine group of peptide nucleic acid, is tagged with the fluorescent tag by incubating with 0.5 to 2 mM, most preferably 1 mM, of fluorescent isothiocyanate in DMF for 30 minutes to 2 hours, most preferably 1 hour, at room temperature, followed by washing with DMF and ethanol sequentially. It is kept in the dark until analyzed by confocal fluorescent laser.

The process for preparing arrays of peptide nucleic acid with various nucleotide sequences by employing polymeric PAG has advantages over prior art as followings:

First, the invented process is desirable in a sense that spin-coating of polymeric PAG dissolved in a proper solvent can be carried out directly, while prior art PPA process employs monomeric PAG mixed with polymeric matrix.

Secondly, the acid generated in PPA process acts separately from the polymeric matrix and the actual amount of acid for deprotecting become less, while PAG itself, in the invented process employing polymeric PAG, contacts with the group to be deprotected and more amount of the acid generated takes part in deprotecting reaction.

Thirdly, PAG can be attached directly to polymeric backbone, which makes PAG become stable to the heat or chemicals generated during the process, assuring that a good quality pattern of a minimum thickness can be obtained without domain formation during coating, which in turn facilitates generation and diffusion of acid by making the exposed light reach the bottom easily.

Fourthly, the process is economical since polymeric PAG can be washed with diluted alkaline solution after patterning.

The present invention is further illustrated by the following examples, which should not be taken to limit the scope of the invention.

EXAMPLE 1

Preparation of Peptide Nucleic Acid Probe

Example 1—1

Attachment of Linker on the Glass Plate

A glass plate for microscope was immersed in cleansing solution (containing 1L of 95% ethanol, water 12 ml, NaOH 120 g), rinsed several times with water and airdried. Then, the glass plate was rinsed with 95% ethanol, immersed in 0.1%(v/v) aminopropyltriethoxysilane in ethanol for 5 minutes at room temperature with agitation, rinsed again with 95% ethanol for three times, and dried in vacuum oven maintained at 120° C. for 20 minutes. And then, the glass plate was placed under argon gas for 12 hours, immersed in DMF, rinsed with dichloromethane, and amine group was fixed on the solid matrix of glass plate for microscope.

Subsequently, 0.5 ml of NMP solution containing 0.1 mM 6-N-t-butoxycarbonyamino caproic acid and 0.2 mM diisopropylethylamine was mixed with NMP solution containing 0.12 mM HATU for 2 minutes. The linker was attached on the surface-derivatized glass plate by immersing the solid matrix prepared above into the said mixed solution for 2 hours at 60° C. with agitation. Then, unreacted amine group was capped with acetyl group by incubating in acetic anhydride/pyridine (1:3, v/v) solution for 1 hour with agitation.

Example 1-2

Attachment of Peptide Nucleic Acid

Polymeric PAG obtained in Preparative Example 2 was dissolved in NMP to reach a final concentration of 30%(w/v), and spin-coated at 3,000 rpm on the glass plate with linker containing acid-labile protecting group prepared in Example 1—1. The coated glass plate was soft-baked for 1 minute at 80° C., exposed to white light with short wavelength using photomask, post baked for 3 minutes at 80° C., and selectively removed the protecting group at the exposed locations by generating acid.

Then, the detached protecting group and the residual polymeric PAG on the glass plate were washed out with 1% trialkylammoniumhydroxide. A solution with 0.3 g of diisopropylethylamine dissolved in NMP solution containing 0.3 g of peptide nucleic acid monomer prepared in Preparative Example 3 and another solution with 0.4 g HATU dissolved in the NMP solution were mixed, and activated for 2 minutes. The glass plate with having its protecting group selectively removed was immersed in the activated solution for 2 hours with agitation, and the peptide nucleic acid monomer was linked to the deprotected amine group on the glass plate. The unreacted amine group was capped with acetyl group by incubating in acetic anhydride/pyridine (1:3, v/v) solution for 1 hour with agitation.

Then, repeating the process of PAG polymeric coating, light exposure using photomask, removal of protection group, reaction of peptide nucleic acid monomer having protected amine group and capping, the peptide nucleic acid on the glass plate was elongated to obtain desired length.

The free reactive group on the glass plate was tagged with fluorescence by incubating with 1 mM of fluorescent isothiocyanate in DMF for 1 hour at room temperature, washed with DMF and ethanol sequentially, dried and kept in the dark. The microscopic image in the 10 μ resolution can be obtained by analyzing the glass plate with spectrofluorimeter.

As clearly described and demonstrated as above, the present invention provides a process for preparing arrays of peptide nucleic acid probe with various nucleotide sequences immobilized on a solid matrix that can be used for DNA chip fabrication. In accordance with the present invention, neutral peptide nucleic acid probes, as the promising substitute for conventional negatively charged oligonucleotide probes, can be prepared by employing polymeric photo-acid generator in a simple and efficient manner, while overcoming the problems confronted in the prior art DNA chip fabrication using PR system and PPA system.

It will be apparent to those skilled in the art that certain changes and modifications can be made to this invention without departing from the spirit or scope of the invention as it is set forth herein.

What is claimed is:

1. A process for manufacturing an array of probes connected to a solid surface, the process comprising:
   providing a substrate having a surface, wherein a functional group protected by an acid-labile protection group is connected to the surface;
   coating a polymeric photoacid generator over the surface connected to the protected functional group, wherein the polymeric photoacid generator is configured to generate an acid when exposed to light;
   exposing the coated polymeric photoacid generator to light so as to generate the acid, whereby the generated acid contacts the acid-labile protection group and deprotects the functional group; and
   reacting the deprotected functional group with a compound comprising an element of a probe, thereby connecting the element of the probe to the surface.

2. The process of claim 1, wherein the provision of the substrate comprises:
   providing a surface without the functional group; and
   modifying the surface so as to connect the functional group protected by the acid-labile protection group.

3. The process of claim 2, wherein the modification of the surface comprises:
   connecting an amino group to the surface as the functional group; and
   protecting the amino group with the acid-labile protection group.

4. The process of claim 3, wherein the protection of the amino group comprises contacting one or more linkers selected from the group consisting of aminoalkylcarboxylic acid, aminoalkoxycarboxylic acid and aminoalkanoylcarboxylic acid with the amino group connected to the surface.

5. The process of claim 3, further comprising capping an unprotected amino group after the protection.

6. The process of claim 5, wherein the capping comprises contacting a compound comprising an acetyl group with the substrate.

7. The process of claim 2, wherein the modification comprises:
   contacting a compound comprising the functional group with the surface to connect the functional group to the surface; and
   further contacting a compound comprising the acid-labile protection group with the surface to protect the functional group.

8. The process of claim 1 wherein the protected functional group is connected to the surface via one or more elements of the probe.

9. The process of claim 1, wherein the surface of the substrate is of organic solvent resistance.

10. The process of claim 1, wherein the substrate is of one or more materials selected from the group consisting of silicon, glass, polyethylene, polypropylene, acrylamide and polymethylmethacrylate.

11. The process of claim 1, wherein the functional group is an amine.

12. The process of claim 1, wherein the acid-labile protection group is one or more selected from the group consisting of t-butyloxycarbonyl, triphenylmethyl, p-anisolyldiphenylmethyl or di(p-anisolyl)monophenylmethyl.

13. The process of claim 1, wherein the deprotection of the functional group is performed over at least a partial area of the surface.

14. The process of claim 1, further comprising enhancing acid generation.

15. The process of claim 14, wherein the enhancing the acid generation comprises heating the substrate before the exposure, after the exposure or both.

16. The process of claim 1, further comprising removal of the generated acid after the exposure of the polymeric photoacid generator to light.

17. The process of claim 1, wherein the exposure of the coated polymeric photoacid generator to light is performed over at least a partial area of the coat of the polymeric photoacid generator.

18. The process of claim 17, wherein the exposure of the coated polymeric photoacid generator to light comprises passing the light through a photomask.

19. The process of claim 18, wherein the photomask is configured to allow passage of the light through one or more predetermined openings.

20. The process of claim 1, further comprising removing the separated protection group from the surface after the exposure of the polymeric photoacid generator to light.

21. The process of claim 1, wherein the probe comprises a sequence of bases selected from the group consisting of adenine, cytosine, guanine, thymine and uracil.

22. The process of claim 1, wherein the element of the probe comprises one or more bases selected from the group consisting of adenine, cytosine, guanine, thymine and uracil.

23. The process of claim 22, wherein the element further comprises an amino group protected by acid-stable protection group.

24. The process of claim 23 wherein the acid-stable protection group is one or more selected from the group consisting of diphenylmethyloxycarbonyl, benzyloxycarbonyl, p-methoxybenzoyl, benzoyl, phenoxyacetyl, t-butylphenoxyacetyl and isobutanoyl groups.

25. The process of claim 1, wherein the compound comprising the probe element comprises a monomeric peptide nucleic acid.

26. The process of claim 1, further comprising washing the substrate after the deprotection.

27. The process of claim 26, wherein the substrate is washed with an alkaline solution or an organic solvent.

28. The process of claim 1, further comprising capping the deprotected functional group unreacted in the reaction.

29. The process of claim 1, wherein the compound comprising the probe element further comprises a functional group protected by an acid-labile protection group, and wherein the functional group is connected to the element.

30. The process of claim 29, further comprising:
deprotecting the functional group connected to the element that is connected to the surface; and
reacting the deprotected functional group connected to the element with another compound comprising an element of the probe, thereby connecting the element connected to the surface and the other element.

31. An array of probes connected to a solid surface manufactured by the process of claim 1.

32. An intermediate construction of an array of probes connected to a solid surface for producing a biochip, comprising;
a solid substrate having a surface;
an element of a probe connected to the surface, wherein the element is further connected to a functional group protected by an acid-labile protection group; and
a coat of a polymeric photoacid generator over the surface and the element connected to the surface, wherein the polymeric photoacid generator is configured to generate an acid when exposed to light.

33. The construction of claim 32, wherein the surface of the substrate is of organic solvent resistance.

34. The construction of claim 32, wherein the substrate is of one or more materials selected from the group consisting of silicon, glass, polyethylene, polyproyylene, acrylamide and polymethylmethacrylate.

35. The construction of claim 32, wherein the element is connected to the surface via one or more elements of the probe.

36. The construction of claim 35, wherein connection of the element with one or more other elements connected to the surface is in a peptide bond.

37. The construction of claim 32, wherein the probe comprises a peptide nucleic acid (PNA).

38. The construction of claim 32, wherein the probe comprises a sequence of bases selected from the group consisting of adenine, cytosine, guanine, thymine and uracil.

39. The construction of claim 32, wherein the element of the probe comprises one or more bases selected from the group consisting of adenine, cytosine, guanine, thymine and uracil.

40. The construction of claim 39, wherein the element further comprises an amino group protected by acid-stable protection group.

41. The construction of claim 40, wherein the acid-stable protection group is one or more selected from the group consisting of diphenylmethyloxycarbonyl, benzyloxycarbonyl, p-methoxybenzoyl, benzoyl, phenoxyacetyl, t-butylphenoxyacetyl and isobutanoyl groups.

42. The construction of claim 32, wherein an acid generated from the polymeric photoacid generator exists in at least a partial area of the polymeric photoacid generator coat.

43. A process of synthesizing a plurality of chemical compounds on a solid surface, comprising:
providing a solid surface;
modifying the surface so as for a plurality of a functional group protected by an acid-labile protection group is connected to the surface;
coating a layer of polymeric photo-acid generator over the modified surface;
selectively exposing the coated layer to light, whereby the polymeric photo-acid generator generates an acid, which contacts and removes one or more acid-labile protection groups; and
contacting molecules for connecting to the surface with one or more functional groups from which the acid-labile groups are removed.

44. The process of claim 1, wherein the polymeric photoacid generator is a polymer with a molecular weight of about 500 to about 1,000,000, which has sulfonium salt on a backbone or a side chain thereof, and also has an organic photoacid generating group on a side chain thereof to generate acid by the exposure to light.

45. The intermediate construction of claim 32, wherein the polymeric photoacid generator is a polymer with a molecular weight of about 500 to about 1,000,000, which has sulfonium salt on a backbone or a side chain thereof, and also has an organic photoacid generating group on a side chain thereof to generate acid by the exposure to light.

46. The process of claim 43, wherein the polymeric photo-acid generator is a polymer with a molecular weight of about 500 to about 1,000,000, which has sulfonium salt on a backbone or a side chain thereof, and also has an organic photo-acid generating group on a side chain thereof to generate acid by the exposure to light.

* * * * *